United States Patent [19]
Gerber

[11] Patent Number: 5,325,864
[45] Date of Patent: Jul. 5, 1994

[54] DIAGNOSTIC TESTING DEVICE FOR THE SKIN

[76] Inventor: Jan Gerber, Bartokhof 23, 2402 GC Alphen aan de Rijn, Netherlands

[21] Appl. No.: 960,363
[22] PCT Filed: Jul. 18, 1991
[86] PCT No.: PCT/NL91/00129
 § 371 Date: Jan. 13, 1993
 § 102(e) Date: Jan. 13, 1993
[87] PCT Pub. No.: WO92/01421
 PCT Pub. Date: Feb. 6, 1992

[30] Foreign Application Priority Data

Jul. 20, 1990 [NL] Netherlands .................... 9000167

[51] Int. Cl.⁵ .............................. A61B 10/00
[52] U.S. Cl. ...................... 128/743; 604/289
[58] Field of Search ........... 128/743; 604/289, 306, 604/367

[56] References Cited

U.S. PATENT DOCUMENTS

| | | | |
|---|---|---|---|
| 2,235,436 | 3/1941 | Laub | 128/743 |
| 3,515,126 | 6/1970 | Fregert | 128/743 |
| 3,894,531 | 7/1975 | Saunders, Jr. | 128/743 |
| 4,214,592 | 7/1980 | Jacquet et al. | 128/743 |
| 4,341,208 | 7/1975 | Gordon . | |
| 4,450,845 | 5/1984 | Engel | 128/743 |
| 4,473,083 | 9/1984 | Maganias | 128/743 |
| 4,788,971 | 12/1988 | Quisno | 128/743 |
| 4,887,611 | 12/1989 | Rudiger et al. | 128/743 |

FOREIGN PATENT DOCUMENTS

| | | |
|---|---|---|
| 0006158 | 9/1980 | European Pat. Off. . |
| 2802413 | 7/1978 | Fed. Rep. of Germany ...... 128/743 |
| 8701577 | 2/1989 | Netherlands . |
| 1459262 | 12/1976 | United Kingdom . |
| 2165756 | 4/1986 | United Kingdom . |
| 2180756 | 4/1987 | United Kingdom . |

Primary Examiner—Max Hindenburg
Attorney, Agent, or Firm—Young & Thompson

[57] ABSTRACT

A diagnostic testing device for the skin, comprising at least one compartment (3) for the accommodation of a diagnostic aid, and adhesive strip (1) on which the compartment is accommodated, and a removable protective strip (4) which is stuck to the adhesive strip at the same side as the compartment. The protective strip is provided with an opening (7) at the position of each compartment.

9 Claims, 3 Drawing Sheets

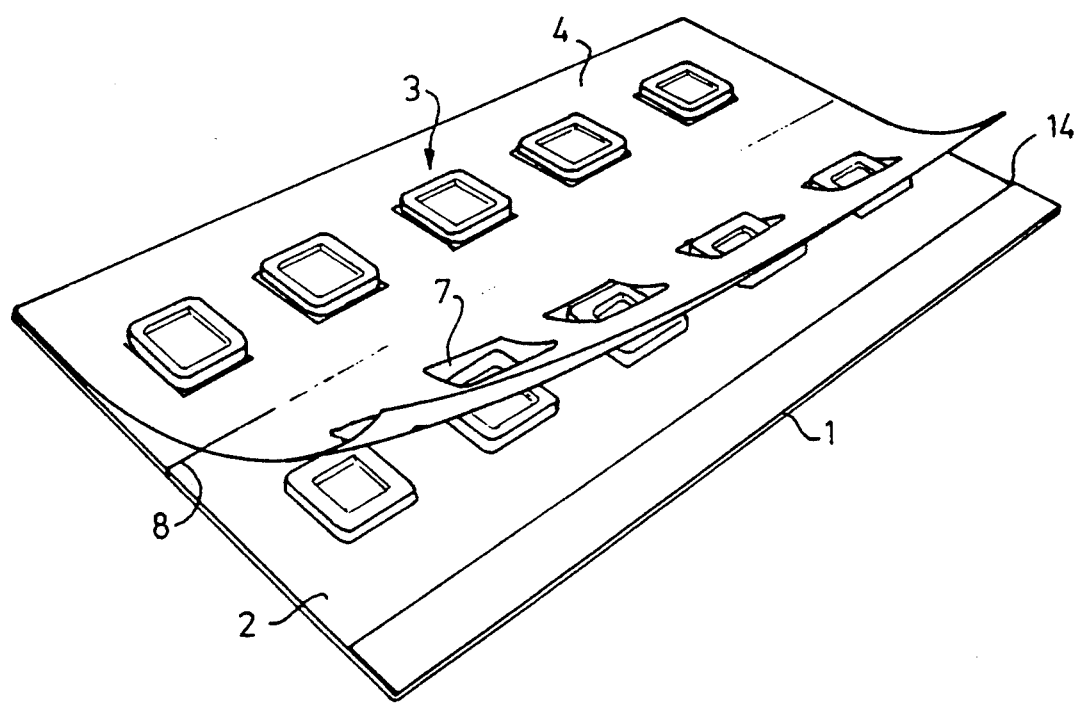

DIAGNOSTIC TESTING DEVICE FOR THE SKIN

FIELD OF THE INVENTION

The invention relates to a diagnostic testing device for the skin, comprising at least one compartment for the accommodation of a diagnostic aid, an adhesive strip on which the compartment is accommodated, and a removable protective strip which is stuck to the adhesive strip at the same side as the compartment.

BACKGROUND OF THE INVENTION

Such a testing device is known from Dutch Application 8,701,577. It is intended for testing the allergic reaction of the skin test subject to various test substances and test liquids. These test substances and test liquids are each accommodated in a compartment of the testing device, which can be applied by means of the adhesive strip to a specific position on the skin of a test subject. The test substances and test liquids are left to act on the skin for a predetermined period, e.g. 72 hours, following which the testing device is removed again.

Since the test substances and test liquids are held captive between the skin and the compartments in question during the test, the influence of the individual different substances can be determined accurately.

In practice, the known testing device is used as follows: First of all, the removable protective strip adhering to the adhesive strip is removed. The various test substances and test liquids are then placed in the compartments which have now become free, following which the whole combination is stuck on the skin of a test subject by means of the adhesive strip. In the process the test substances and test liquids in the compartments come into contact with the part of the skin which is covered by the compartment in question. This last factor is very important for accurately determining the influence on the skin of each of the various substances individually.

However, with the use of this known testing device the problem occurs that the placing of the test substances and test liquids in the compartments does not always take place equally accurately, owing to the inaccuracy of the metering devices/hypodermic needle holders for the substances and phials for the liquids. The test substance or test liquid is sometimes spilled on the adhesive strip, as a result of which the allergic reaction does not remain limited to the "test area" and the adjacent skin can also be affected. If another substance also happens to be spilled on the adhesive strip, there is a risk of the various substances becoming mixed, which means that a reliable result can no longer be obtained. Besides, in such a case the test can no longer reasonably be carried out, because the adhesive layer of the plaster has lost its effectiveness.

SUMMARY OF THE INVENTION

The object of the invention is therefore to provide a diagnostic testing device of the type described above, which does not have this disadvantage, and in the case of which it can always be ensured that the test substances and test liquids are situated only in their appropriate compartments. This is achieved according to the invention in that at the position of each compartment the protective strip is provided with an opening corresponding essentially to the compartment. This means that the compartments are accessible through the protective strip, while the whole of the remaining part of the adhesive strip is screened off by the protective strip.

If a certain part of the test substances and test liquids is spilled during placing in the compartments, this part falls onto the protective strip. Before the testing device is applied to the skin, the protective strip is removed, in which case any test substances and test liquids spilled on it are also removed. The exposed adhesive strip is completely free of spilled substances, and compartments filled with test substances and test liquids in the correct manner can be applied directly to the skin. In the case of the testing device according to the invention it is therefore ensured at all times that the skin is brought into contact with the various test substances and test liquids only at the position of the compartments. The user-friendliness of the testing device is consequently considerably greater than that of the known device both for the wearer and the doctor or his or her assistant. The product is also easier to handle due to the fact that the adhesive layer is in fact exposed only when the testing device is applied to the skin.

Each compartment preferably has a plate-shaped bottom which is fixed to the adhesive strip and has a raised edge surrounding the bottom, and each opening in the protective strip is of a shape corresponding to the periphery of the edge. The compartments in this case project with their edge through the protective strip.

In practice, several substances are preferably tested simultaneously. For this, one or more rows of compartments are provided on the adhesive strip, and the protective strip has a corresponding number of rows of openings.

The compartments are preferably not interconnected, in such a way that the protective strip rests over its entire surface against the adhesive strip. In the case of the unknown testing device the compartments are interconnected by bridges, which means that the protective strip cannot rest against the adhesive strip at that point. According to the invention, it is now ensured that the whole surface of the adhesive strip outside the compartments is protected against drying out, in such a way that good adhesion of the adhesive strip to the skin can be obtained.

As regards the known product, the philosophy is that the compartment must be of such a capacity that it can hold at least 100 microliters of test substance/test liquid. If it is a solution in water, the compartment preferably contains a carrier material, such as a piece of filter paper for absorbing the test liquid. In the case of test materials which are not water-soluble, the test material is placed in the test compartment as a mixture with vaseline.

It has been found that it is sufficient to place only half or almost a quarter of the quantity of test substrate used hitherto in the compartments of the testing device according to the invention. In this way a good test result is obtained with a quantity of, for example, 30 $\mu$l.

The shape of the raised edge of the compartments must be such that after placing on the skin a good containment is achieved. It goes without saying that leakage of the compartments after application to the skin produces undesirable reactions of the skin and makes assessment of the test result difficult.

The edge of the compartments is to this end preferably rounded off in cross-section, the rounding being stronger on the inside of the edge than on the outside.

An advantage of the rounding on the outside of the edge is a greater comfort for the wearer. In this respect an even greater improvement can be obtained if the plate is square and has rounded corner points, and the edges have correspondingly rounded corner points.

In an alternative embodiment, it is known to dispose a layer provided with at least one opening on the adhesive strip, which opening together with the adhesive strip forms a compartment. The invention can also be used in this testing device by ensuring that the openings in the layer coincide with the openings in the protective strip.

The compartments can be protected from external influences before use by providing a covering, detachable cover strip at the sides facing away from the adhesive strip.

BRIEF DESCRIPTION OF THE DRAWINGS

The invention will be explained in greater detail below with reference to the drawings, wherein:

FIG. 4 shows a view in perspective of the testing device according to another embodiment of the invention.

DETAILED DESCRIPTION OF THE INVENTION

Figure 1:
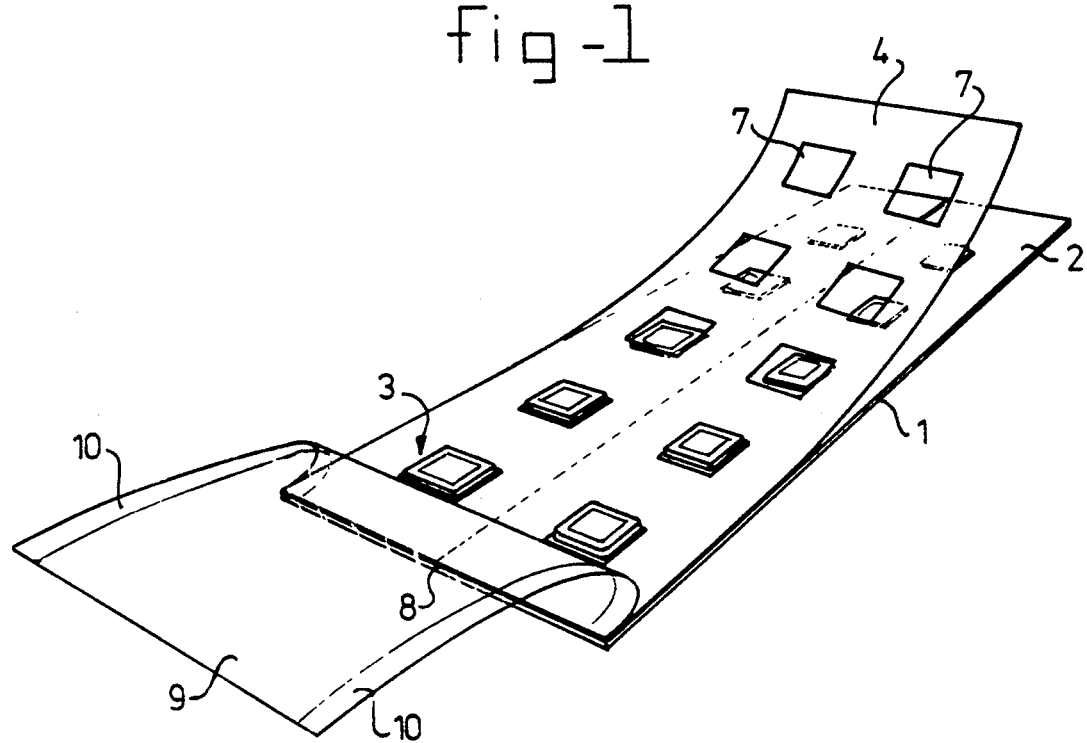
FIG. 1 shows a view in perspective of the testing device according to the invention, in which the protective strip is partially removed.
Figure 2:
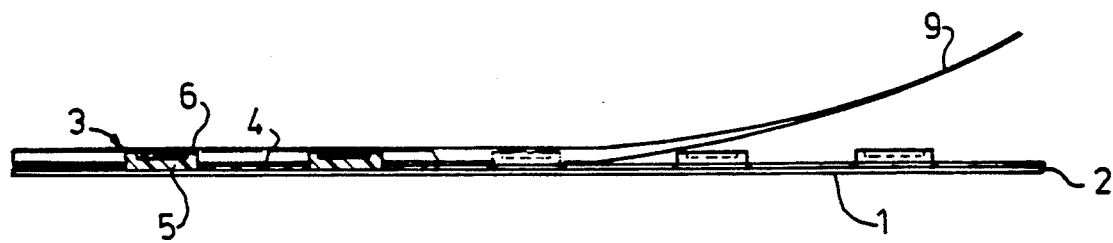
FIG. 2 shows a side view, partially in cross-section, of the device according to FIG. 1.

The device shown in FIGS. 1 and 2 comprises an adhesive strip 1, to which an adhesive 2 is applied. A number of compartments 3 are applied in the same way as the adhesive 2, said compartments having a bottom 5 and a raised edge 6 surrounding it. A test substance, which may or may not be applied to a piece of filter paper, is placed in the recess formed by the bottom 5 and the raised edge 6.

A protective strip 4, to protect the adhesive 2 from drying out, is applied to the adhesive layer 2 of the adhesive strip 1. The protective strip 4 is provided with openings 7, the position and dimensions of which correspond to those of the compartments 3. It will be clear that when a test substance is being placed in the various compartments a quantity of substance may be spilled on the protective strip 4, and will not reach the adhesive strip 1. As soon as the protective strip 4 is then removed from the adhesive strip 1, the spilled substance is also removed, with the result that an entirely clean adhesive strip 1 remains and can be applied directly to the skin.

A detachable cover strip 9, which is joined to the protective strip 4 by means of adhesive edges 10, can be provided on the top of the compartments 3. The compartments 3 are in this way protected well from external influences before use.

The testing device also has a lengthwise running dividing line 8, in such a way that two rows of five compartments each, with their own adhesive strip can be formed.

Figure 3:
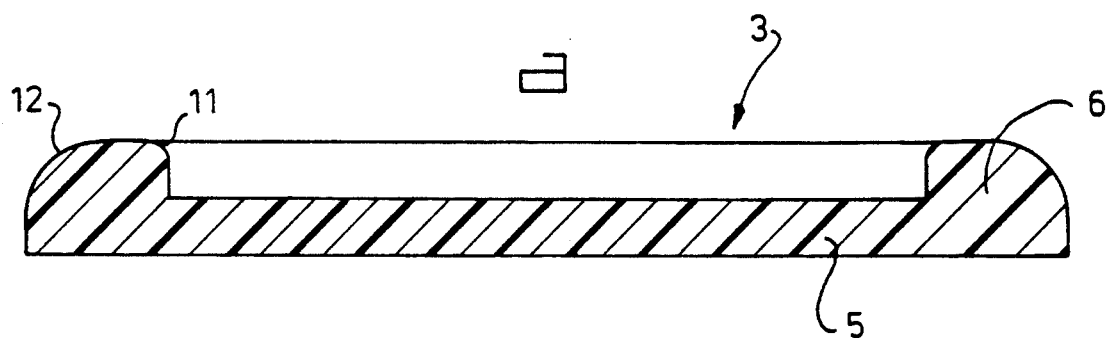
FIGS. 3a, 3b show details of a compartment.
Figure 3:
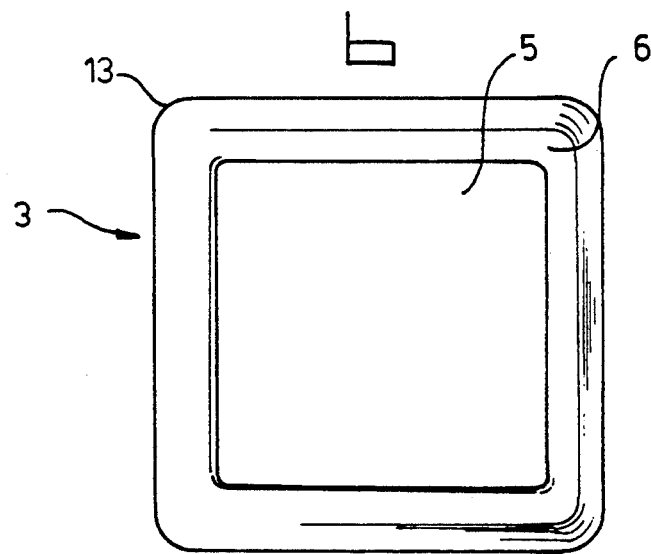

In the compartment shown in FIGS. 3a and 3b the edge 6 is designed in cross-section with a fairly great curvature on the inside 11, for example with a radius of curvature of 0.2 mm. The curvature on the outside 12 is less great, for example having a radius of curvature of 0.8 mm.

In top view the corners 13 of the compartment are rounded. The rounded corners provide the wearer with greater comfort.

FIG. 4 shows a view in perspective of the testing device according to the invention, in which the protective strip 4 is provided with a cut 14 near one of its perpheral sides. This cut 14 makes it possible to remove the protective strip easily in two parts from the adhesive strip. Of course, it is also possible for the protective strip to be provided with a cut which is in the center for example, and not near one of its peripheral sides. However, the latter embodiment has the disadvantage that, due to the weight of the compartments, the device has a tendency to sag along the lengthwise side at the position of the cut. This is undesirable, because a rounding in the device, which generally arises towards the side where the cut is situated, detaches the protective strip to some extent from the adhesive material, which consequently deteriorates in quality through oxidation.

The test plaster can have rounded corners which increase the comfort for the wearer.

The adhesive strip is preferably provided with an adhesive which is readily tolerated by the skin. A porous acrylate copolymer which can be tolerated by the skin is preferably used. The use of an adhesive which is resistant to perspiration (so-called wet stick adhesives) is recommended.

The adhesive strip generally comprises a non-woven textile or plastic material and is, for example, colour corresponding to the colour of the skin.

The present invention is explained with reference to a diagnostic testing device, in which the compartments have a square plate-shaped bottom with corresponding edges. Instead of being square, the compartments can, however, be of any desired shape, and can be, for example, round or oval.

The advantages of the testing device according to the invention can be summarized as follows:

In the case of the known products the adhesive strip is to a greater or lesser extent detached from the protective strip, as a result of the height of the raised edge of the compartments. This means that in a small region around each compartment oxygen comes into contact with the adhesive on the adhesive strip. After a few weeks (of storage) have passed, the adhesive force is greatly reduced, as a result of the oxidation which has occurred. Through the perforation of the protective strip at the position of the compartments, the device according to the invention can be kept for a long time, for example a year. The protective strip lies completely tightly on the adhesive layer of the strip around each compartment. Premature oxidation of the adhesive layer is consequently absolutely impossible.

Devices of the present type without protective strip are difficult to handle. Such a device "hangs" over the palm of the hand and the fingers, while at the same time the compartments must be filled with a specified quantity of test substance or test liquid using injection devices which in practice meter poorly. In the case of the device according to the invention the protective strip need not be removed before the compartments are filled. The firmness of the device as such means that accurate filling of the compartments can be carried out in the optimum way, despite the often inaccurate working of the injection devices.

In the case of the known devices an excess of test substance or test liquid makes the device worthless, because the adhesive force of the adhesive strip is adversely affected. Besides, such an excess causes great inaccuracy of the test results. In the case of the device according to the invention an excess of test preparation can be removed from the protective strip in a simple manner, for example using a cotton bud. This means that an accurate preparation of the test is possible.

The preparation of extensive and large numbers of tests is impossible in the case of the known devices having a protective strip, because on removal of the protective strip the adhesion of the adhesive layer is reduced due to the oxidation discussed above. However, with the device according to the invention large and extensive tests for different patients can be prepared in an excellent manner in one go. The adhesive layer remains in excellent condition due to the continual presence of the protective strip.

The storage of testing devices prepared in advance is not easily possible in the case of the known devices. A large amount of storage space is needed for the devices without protective strip, in order to prevent adhesion between them. The storage of a large number of tests prepared a long way ahead is readily possible with the device according to the invention. In practice, tests are often prepared for a whole week.

The devices according to the present type are often applied for a period of, for example, 72 hours to the skin of the person being tested. In the case of the known device it is often necessary to fix the test plaster additionally by sticking on extra plasters. The device according to the invention makes it possible to carry out 72-hours test with good results without sticking on other plasters. The use of a wet stick adhesive means that the test plaster according to the invention retains its adhesion, even if the test subject perspires heavily.

I claim:

1. Diagnostic testing device for the skin comprising at least one row of compartments, each compartment adapted to contain a diagnostic aid, an adhesive strip on which said at least one row of compartments is located, and a removable protective strip which is stuck to the adhesive strip at the same side as the compartments, said protective strip being provided with an opening at the position of each compartment, and said protective strip having number of rows of openings corresponding to the number of rows of compartments.

2. Testing device according to claim 1, wherein each compartment has a plate-shaped bottom which is fixed to the adhesive strip and has a raised edge surrounding the bottom, and each opening in the protective strip is of a shape corresponding to the periphery of the edge.

3. Testing device according to claim 2, wherein the compartments are not interconnected, and the protective strip rests over its entire surface against the adhesive strip.

4. Testing device according to claim 2, wherein the edge is rounded off in cross section.

5. Testing device according to claim 4, wherein the rounding is greater on the inside of the edge than on the outside.

6. Testing device according to claim 5, wherein the plate is square and has rounded corner points, and the edges have correspondingly rounded corner points.

7. Testing device according to claim 1, wherein a layer provided with at least one opening is situated on the adhesive strip, which opening together with the adhesive strip forms a compartment, and openings in the layer coincide with the openings in the protective strip.

8. Testing device according to claim 1, further including a detachable cover strip for covering the compartments at the side facing away from the adhesive strip.

9. Testing device according to claim 1, wherein the protective strip has a cut near one of its peripheral sides.

* * * * *